US00PP33611P2

(12) United States Plant Patent
Snijder

(10) Patent No.: US PP33,611 P2
(45) Date of Patent: Nov. 2, 2021

(54) *PELARGONIUM* PLANT NAMED 'PEPZ0012'

(50) Latin Name: *Pelargonium peltatum*
Varietal Denomination: PEPZ0012

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/091,948

(22) Filed: Nov. 6, 2020

(51) Int. Cl.
*A01H 6/42* (2018.01)
*A01H 5/02* (2018.01)

(52) U.S. Cl.
USPC ..... Plt./332

(58) Field of Classification Search
USPC ..... Plt./332
See application file for complete search history.

(56) References Cited

PUBLICATIONS

PLUTO Plant Variety Database Mar. 12, 2021 p. 1.*

* cited by examiner

*Primary Examiner* — Annette H Para
(74) *Attorney, Agent, or Firm* — Dale Skalla

(57) ABSTRACT

A new *Pelargonium* plant named 'PEPZ0012' particularly distinguished by a mounding-spreading plant habit, medium green foliage with light zonation, semi-double, pink flowers with a white bi-color patterning on large umbels.

1 Drawing Sheet

Latin name of the genus and species of the plant claimed: *Pelargonium peltatum*.

Varietal denomination: 'PEPZ0012'.

BACKGROUND OF THE NEW PLANT

The present invention comprises a new *Pelargonium*, botanically known as *Pelargonium peltatum*, and hereinafter referred to by the variety name 'PEPZ0012'.

'PEPZ0012' is a product of a spontaneous mutation. The new cultivar 'PEPZ0012' has a mounding-spreading plant habit, medium green foliage with light zonation, semi-double, pink flowers with a white bi-color patterning on large umbels.

'PEPZ0012' originates from a spontaneous mutation of a plant of *Pelargonium peltatum* 'Lulumex' (U.S. Plant Pat. No. 13,022) in May 2015, in a greenhouse in Germany 'Lulumex' has bicolor purple-white florets while 'PEPZ0012' has bicolor pink-white florets.

The first act of asexual reproduction of 'PEPZ0012' was accomplished when vegetative stem cuttings were propagated from the initial selection in June 2015 in a greenhouse in Enkhuizen, The Netherlands.

BRIEF SUMMARY OF INVENTION

Horticultural examination of plants grown from cuttings of the plant initiated in June 2015 in Enkhuizen, The Netherlands and continuing thereafter, has demonstrated that the combination of characteristics as herein disclosed for 'PEPZ0012' are firmly fixed and are retained through successive generations of asexual reproduction.

'PEPZ0012' has not been observed under all possible environmental conditions. The phenotype may vary significantly with variations in environment such as temperature, light intensity, and day length.

'PEPZ0012' has not been made publicly available prior to the effective filing date of this application, notwithstanding any disclosure that may have been made less than one year prior to the effective filing date of this application by the inventor or another who obtained 'PEPZ0012' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEPZ0012' with colors being as true as possible with an illustration of this type.

Figure 1:
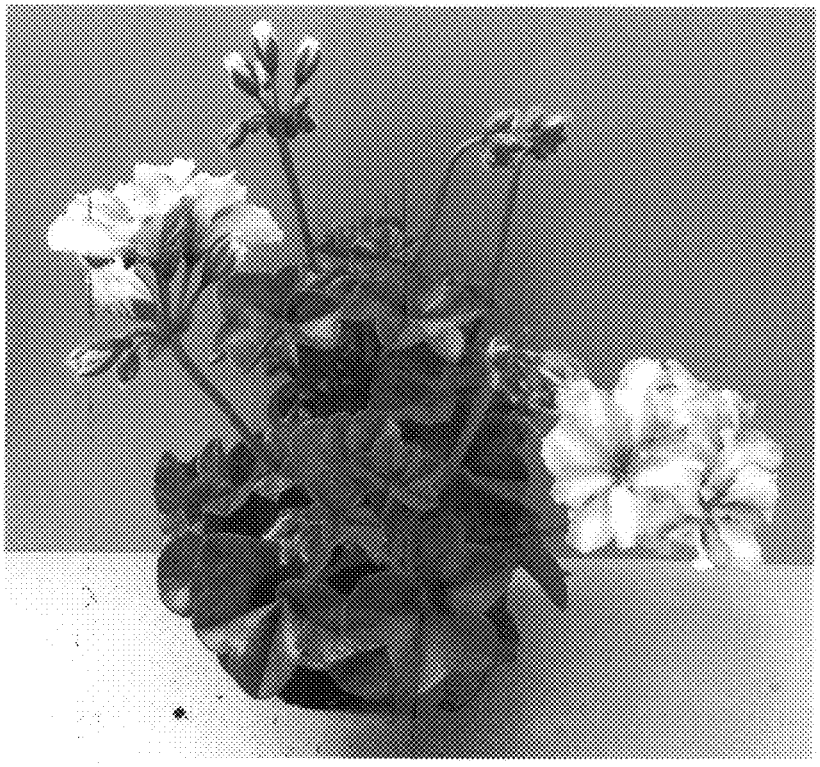
Figure 2:
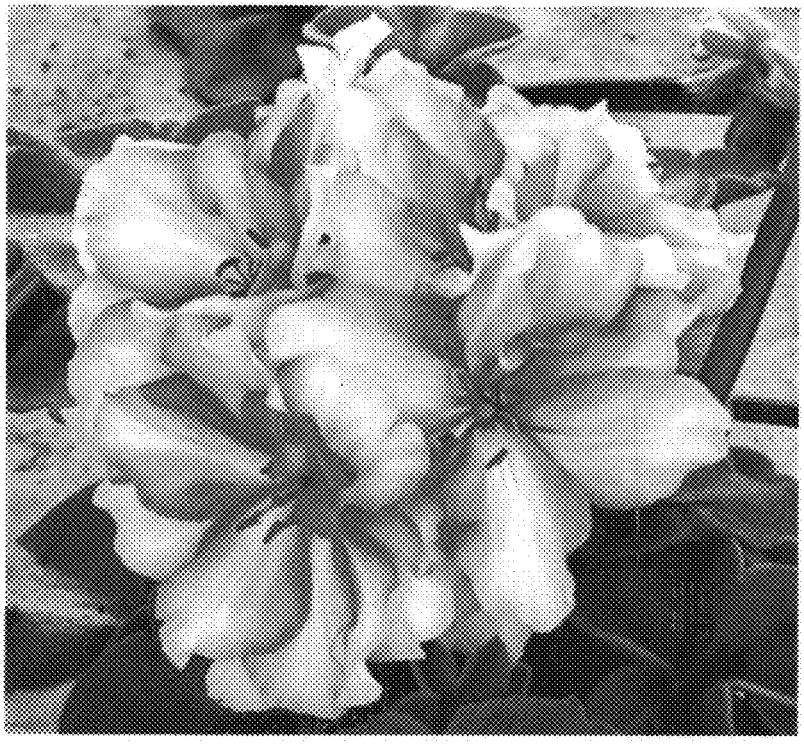

The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in early July 2020 under natural light. These plants were approximately 13 weeks old and were grown in a 12 cm pots, in a greenhouse trial. The plant shown in the photograph is about 12 weeks old growing in a 12 cm pot in a greenhouse in Andijk, The Netherlands. The photographs were taken in March 2019.

Color references are made to The Royal Horticultural Society Colour Chart (RHS) 2001.

TABLE 1

DIFFERENCES BETWEEN THE NEW VARIETY 'PEPZ0012' AND A MOST SIMILAR VARIETY

| | 'PEPZ0012' | 'Free Arcred' (U.S. Plant Pat. No. 15,651) |
|---|---|---|
| Corolla color: | Rose pink edge and white center | Dark red edge and white center |

Plant:
- *Form, growth and habit.*—Upright-mounding growth habit.
- *Plant height.*—14-19 cm.
- *Plant height (inflorescence included).*—20-25 cm.
- *Plant width.*—13-15 cm.

Roots:
- *Number of days to initiate roots.*—15-18 days at about 22 degrees C.
- *Number of days to produce a rooted cutting.*—21-23 days at 22 degrees C.
- *Type.*—Fine, fibrous, free branching.
- *Color.*—RHS N155B but whiter.

Foliage:
- *Variegation.*—Absent.
- *Immature leaf, color upper surface.*—Closest to RHS 138A.
- *Immature leaf, lower surface.*—Closest to RHS 138B.
- *Mature leaf, color upper surface.*—Closest to RHS 137B.
- *Mature leaf, color lower surface.*—Closest to RHS 137D.
- *Length.*—4-7 cm.
- *Width.*—7-9 cm.
- *Shape.*—Cordate.
- *Base shape.*—Cordate.
- *Apex shape.*—Acute.
- *Margin.*—Slightly dentate.
- *Texture upper side.*—Hirsute.
- *Texture lower side.*—Hirsute.
- *Leaf zonation color.*—Medium distinct, about RHS 166A.
- *Color of veins, upper surface.*—RHS 137B, largely indistinct.
- *Color of veins, lower surface.*—RHS 137D, largely indistinct.
- *Petiole color.*—RHS 143C.
- *Petiole length.*—4-5 cm.
- *Diameter of petiole.*—0.2 cm.
- *Texture.*—Pilose, hirsute, glandular hairs.

Stem:
- *Quantity of branches.*—10.
- *Color of stem.*—RHS 144A and RHS 144B.
- *Length of stem.*—10-13 cm.
- *Diameter.*—0.4 cm.
- *Length of internodes.*—2.5-3.5 cm.
- *Texture.*—Sparsely hirsute, pilose, glandular hairs.

Peduncle:
- *Color of peduncle.*—RHS 143A.
- *Length of peduncle.*—9-11 cm.
- *Peduncle diameter.*—0.3-0.5 cm.
- *Texture.*—Hirsute, glandular hairs.

Pedicel:
- *Color of pedicel.*—RHS 144A, slightly mottled RHS 179B.
- *Length of pedicel.*—2.5-3.5 cm.
- *Diameter of pedicel.*—0.15-0.2 cm.
- *Texture.*—Sparsely pilose, glandular hairs.

Bud (just before opening):
- *Color.*—Outside of bud RHS 145C, with edges of petals RHS 63C.
- *Length.*—1.4-1.5 cm.
- *Width.*—0.8-1.2 cm including sepals.
- *Shape.*—Elliptical.

Inflorescence:
- *Type.*—Umbel; semi-spherical or nearly semi-spherical.
- *Lastingness of individual flowers.*—7-9 days at 18° C. temperature.
- *Number of inflorescences per plant.*—6-12, with 3-7 immature umbels in various stages.
- *Fragrance.*—None.
- *Umbel diameter.*—8-9 cm.
- *Umbel depth.*—7-9 cm.

Corolla:
- *Form.*—Semi-double.
- *Number of petals.*—12-18.
- *Diameter of flower.*—5-5.5 cm.
- *Depth of flower.*—1.5-2 cm.
- *Color upper petals, upper surface.*—Between RHS 65D and N155C at apex and in center of the petal, coloring towards RHS N66C at edges, with stripes RHS N66A towards the base.
- *Color upper petals, lower surface.*—Largely between RHS 65D and RHS N155C, fading to RHS 65A towards the base.
- *Length of upper petals.*—3-3.3 cm.
- *Width of upper petals.*—1.8-2.1 cm.
- *Color lower petals, upper surface.*—Between RHS 65D and RHS N155C at apex and in center of the petal, coloring towards RHS N66C at edges.
- *Color lower petals, lower surface.*—Largely between RHS 65D and RHS N155C, fading to RHS 65A towards the base.
- *Length of lower petals.*—2.7-3 cm.
- *Width of lower petals.*—2-2.2 cm, petaloids variably smaller and with variable shape.
- *Petal shape.*—Obovate to spathulate.
- *Apex shape.*—Rounded.
- *Margin.*—Entire.
- *Base.*—Attenuate.
- *Petal texture.*—Papillose on both surfaces.

Calyx:
- *Number of sepals.*—5-6.
- *Color of sepals.*—RHS 143C.
- *Length of sepals.*—1.1-1.4 cm.
- *Width of sepals.*—0.2-0.4 cm.
- *Sepal shape.*—Lanceolate to linear.
- *Apex shape.*—Acute.
- *Margins.*—Mostly fused.
- *Texture, upper surface.*—Glabrous.
- *Lower surface.*—Glandular hairs, hirsute.

Reproductive organs:

Gynoecium:
- *Pistil.*—1.
- *Length.*—1-1.2 cm.
- *Style color.*—RHS N155D.
- *Style length.*—0.2-0.3 cm.
- *Stigma color.*—RHS N79C.
- *Ovary color.*—RHS 144A, mottled RHS 183A.
- *Ovary length.*—0.4-0.5 cm.
- *Ovary diameter.*—0.2 cm.

Androecium:

*Number of stamens.*—5-7 with 1-6 staminoids.

*Color of filaments.*—RHS N155D fading to N155C at the apex.

Length filaments.—0.3-0.8 cm.

*Anther color.*—RHS 64D.

*Length of anthers.*—0.3 cm.

*Color of pollen.*—RHS 169A.

*Pollen amount.*—Scarce.

*Fertility/seed set.*—Has not been determined to date.

*Disease/pest resistance.*—Has not been determined to date.

What is claimed is:

1. A new and distinct variety of *Pelargonium* plant named 'PEPZ0012' substantially as illustrated and described herein.

* * * * *